United States Patent [19]

Leach et al.

[11] 3,993,701

[45] Nov. 23, 1976

[54] METHYLATION OF α-NAPHTHOL TO 2-METHYL-1-NAPHTHOL

[75] Inventors: Bruce E. Leach; Charles M. Starks, both of Ponca City, Okla.

[73] Assignee: Continental Oil Company, Ponca City, Okla.

[22] Filed: Aug. 25, 1975

[21] Appl. No.: 607,735

[52] U.S. Cl. .............................. 260/621 R
[51] Int. Cl.² ................................ C07C 39/14
[58] Field of Search ........ 260/621 R, 624 C, 624 R, 260/619 F

[56] References Cited
UNITED STATES PATENTS 3,426,358  2/1969  Schlichting ..................... 260/621 R
3,707,569  12/1972  Van Sorge ..................... 260/621 R

FOREIGN PATENTS OR APPLICATIONS 1,817,342  9/1970  Germany ........................ 260/621 R

*Primary Examiner*—James O. Thomas, Jr.
*Assistant Examiner*—W. B. Lone
*Attorney, Agent, or Firm*—Cortlan R. Schupbach, Jr.

[57] ABSTRACT

α-Naphthol is methylated using methanol to form 2-methyl-1-naphthol over a catalyst bed of alumina. The reaction provides high selectivity to 2-methyl-1-naphthol. Alumina catalysts derived from alumina alkoxide hydrolysis are preferred.

6 Claims, No Drawings

METHYLATION OF α-NAPHTHOL TO 2-METHYL-1-NAPHTHOL

This invention relates to the production of 2-methyl-1-naphthol. More specifically, this invention relates to a method for the production of 2-methyl-1-naphthol from easily obtainable α-Naphthol using readily available alumina catalysts.

2-Methyl-1-naphthol is a useful intermediate in the preparation of 2-methyl-1,4-naphthoquinone, also known as Vitamin K3. This quinone, also known as Menadione, is an important anti-hemorrhaging agent. Menadione is also used as an intermediate in the preparation of Vitamins K1 and K2. The starting material for Menadione preparation currently is believed to be 2-methyl-naphtholene as disclosed in *The Chemistry of the Vitamins*, Interscience New York, by S. F. Dyke, 1965, page 322.

Some prior art publications, such as German Pat. Nos. 1,817,342, 1,817,343; U.S. Pat. No. 3,126,331, have suggested the possibility of liquid phase methylation of naphthols but set forth no guidelines or examples. It would be a definite advantage to use 2-methyl-1-naphthol as a starting material for the preparation of 2-methyl-1,4-naphthoquinone since its oxidation would not be complicated by attacks at positions on the ring other than the position desired.

It is therefore an object of the present invention to provide a method for the preparation of 2-methyl-1-naphthol from α-naphthol. Other objects will become apparent to those skilled in this art as the description proceeds.

In accordance with the object of the present invention, there is now provided a method for methylating α-naphthol in high selectivity to 2-methyl-1-naphthol under liquid phase conditions. The reaction is carried out at temperatures of from about 320° to about 380° C under pressures of from about 300 to about 500 pounds per square inch gauge (psig) and a methanol:α-naphthol mol ratio of from about 0.1 to about 1.0. When carried out over a catalyst bed, the reaction has a liquid hourly space velocity (LHSV) of from 1 to 10. The catalyst used is an alumina catalyst.

Preferred conditions are temperatures of from 340° to about 360° C, pressures of from 350 to 450 psig, mol ratios of from 0.2 to 0.8, and LHSV of from 2 to about 6. Preferred catalysts are those aluminas derived from aluminum alkoxide hydrolysis procedures. Representative examples of such catalysts are the CATAPAL and DISPAL aluminas manufactured by the Continental Oil Company.

Diluents can be used to make a liquid feed at moderate temperatures but is not necessary to the reaction. Diluents useful in the process of the present invention are those which allow a liquid feed to the reactor but do not react or interfere with the reaction. Representative examples of such diluents are water and liquid aromatics, such as toluene, xylenes, mesitylene, and naphthalene.

The reaction is more concretely described with reference to the example below, wherein all parts and percentages are by weight unless otherwise specified. The example is intended to exemplify the present invention and not to limit it.

The reaction was carried out in ⅜-inch stainless steel reactors containing approximately 15 cubic centimeters of catalyst, the catalyst being CATAPAL SB alumina extrudate, 1/16 inch in diameter. The α-naphthol was mixed with 0.5 mol ratio of methanol and diluted with toluene to make a liquid feed. The feed was pumped through the described reactor at LHSV of 3 and a back pressure of 400 psig. Temperature runs ranging from 340° to 355° C were carried out. The products were analyzed by gas-liquid chromatography and identified by nuclear magnetic resonance and mass spectroscopy. The results are shown in Table I.

TABLE I

LIQUID PHASE METHYLATION OF α-NAPHTHOL

| Component | TEMPERATURE (° C) | | | |
|---|---|---|---|---|
| | 340 | 340 | 345 | 350 |
| Light Ends | 1.85 | 1.20 | 1.35 | 2.31 |
| 1-Methoxynaphthol | 0.70 | 1.41 | 2.88 | 2.67 |
| 1-Naphthol | 59.39 | 61.10 | 56.23 | 50.67 |
| 2-Methyl-1-Naphthol | 32.95 | 32.27 | 36.50 | 40.70 |
| Higher Methylated Products | 5.10 | 3.64 | 3.04 | 3.60 |

The component identified in Table I as light ends includes methanol and dimethyl ether. The components identified as higher methylated products are tri and tetra methylated compounds having high boiling points.

It can be seen from the Table I data presented that up to 50 percent conversion of the 1-naphthol can be obtained and of the products converted, over 82 percent selectivity to 2-methyl-1-naphthol is obtainable.

Separation of the 2-methyl-1-naphthol from by-products can be accomplished by techniques well known to those skilled in this art, such as fractional distillation. Following removal of the 2-methyl-1-naphthol from other reaction products, unreacted α-naphthol can be recycled to methylation. The 2-methyl-1-naphthol so obtained will be sufficiently pure for most uses; however, further purification can be accomplished by well-known techniques, such as crystallization.

While certain embodiments and details have been shown for the purpose of illustrating this invention, it will be apparent to those skilled in this art that various changes and modifications may be made herein without departing from the spirit or the scope of the invention.

We claim:

1. A process for the production of 2-methyl-1-naphthol comprising reacting alpha-naphthol with methanol in liquid phase over alumina catalysts, wherein the reaction is carried out at a temperature of from about 320° C to 380° C, pressures of from about 300 psig to 500 psig, and a methanol/alpha-naphthol mole ratio of from about 0.1 to about 1.0.

2. A process as described in claim 1 wherein the reaction is carried out in a continuous flow reactor at a liquid hourly space velocity (LHSV) of from 1 to 10.

3. A process as described in claim 1 wherein the α-naphthol/methanol is diluted with an unreactive diluent selected from the group consisting of liquid aromatics, such as toluene, xylenes, mesitylene, and napthalene and water, prior to carrying out the reaction.

4. A process as described in claim 1 wherein the alumina catalyst used is derived from aluminum alkoxide hydrolysis.

5. A process as described in claim 1 wherein 2-methyl-1-naphthol is obtained from the reaction product by fractional distillation.

6. A process as described in claim 1 wherein unreacted α-naphthol is recycled for methylation.

* * * * *